(12) United States Patent
Henderson et al.

(10) Patent No.: US 10,413,667 B2
(45) Date of Patent: Sep. 17, 2019

(54) AUTOINJECTOR

(71) Applicant: SANOFI-AVENTIS DEUTSCHLAND GMBH, Frankfurt am Main (DE)

(72) Inventors: Charley Henderson, Cambridgeshire (GB); David Cross, Hertfordshire (GB); Douglas Ivan Jennings, Hertfordshire (GB); Ryan Anthony McGinley, Cambridgeshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 931 days.

(21) Appl. No.: 14/421,020

(22) PCT Filed: Aug. 12, 2013

(86) PCT No.: PCT/EP2013/066775
§ 371 (c)(1),
(2) Date: Feb. 11, 2015

(87) PCT Pub. No.: WO2014/026937
PCT Pub. Date: Feb. 20, 2014

(65) Prior Publication Data
US 2015/0290392 A1 Oct. 15, 2015

(30) Foreign Application Priority Data

Aug. 15, 2012 (EP) .................................... 12180577

(51) Int. Cl.
*A61M 5/20* (2006.01)
*A61M 5/315* (2006.01)
(Continued)

(52) U.S. Cl.
CPC ............ *A61M 5/20* (2013.01); *A61M 5/3204* (2013.01); *A61M 5/427* (2013.01);
(Continued)

(58) Field of Classification Search
CPC .... A61M 2005/206; A61M 2005/2496; A61M 2005/3151; A61M 5/427; A61M 5/32048
See application file for complete search history.

(56) References Cited

U.S. PATENT DOCUMENTS

| 3,388,863 A | 6/1968 | Andersen et al. |
| 3,712,301 A | 1/1973 | Sarnoff |

(Continued)

FOREIGN PATENT DOCUMENTS

| EP | 2238999 | 10/2010 |
| EP | 2468340 | 6/2012 |

(Continued)

OTHER PUBLICATIONS

International Preliminary Report on Patentability in International Application No. PCT/EP2013/066775, dated Feb. 17, 2015, 8 pages.

(Continued)

*Primary Examiner* — Jenna Zhang
(74) *Attorney, Agent, or Firm* — Fish & Richardson P.C.

(57) ABSTRACT

Described is an autoinjector comprising of a case, a motor adapted to rotate a drive gear, and a curvi-linear plunger adapted to mate with the drive gear. The plunger includes a distal end with a resilient flange, which in a non-deflected state, abuts a proximal collar of a syringe, and, in a deflected state, advances through the proximal collar and engages a stopper in the syringe.

15 Claims, 10 Drawing Sheets

Specification includes a Sequence Listing.

(51) Int. Cl.
  *A61M 5/42* (2006.01)
  *A61M 5/50* (2006.01)
  *A61M 5/46* (2006.01)
  *A61M 5/32* (2006.01)
  *A61M 5/24* (2006.01)
  *A61M 5/31* (2006.01)

(52) U.S. Cl.
  CPC ........... *A61M 5/5086* (2013.01); *A61M 5/326* (2013.01); *A61M 2005/206* (2013.01); *A61M 2005/208* (2013.01); *A61M 2005/2073* (2013.01); *A61M 2005/2407* (2013.01); *A61M 2005/2496* (2013.01); *A61M 2005/3125* (2013.01); *A61M 2005/31518* (2013.01); *A61M 2205/273* (2013.01); *A61M 2205/3368* (2013.01); *A61M 2205/36* (2013.01); *A61M 2205/3606* (2013.01); *A61M 2205/52* (2013.01); *A61M 2205/581* (2013.01); *A61M 2205/582* (2013.01); *A61M 2205/583* (2013.01); *A61M 2205/6054* (2013.01); *F04C 2270/0421* (2013.01)

(56) References Cited

U.S. PATENT DOCUMENTS

| 3,742,948 | A | 7/1973 | Post et al. | |
|---|---|---|---|---|
| 4,493,704 | A * | 1/1985 | Beard | A61M 5/1452 604/154 |
| 7,198,615 | B2 * | 4/2007 | Langley | A61M 5/31513 604/151 |
| 2002/0004651 | A1 * | 1/2002 | Ljunggreen | A61M 5/31501 604/218 |
| 2003/0105430 | A1 * | 6/2003 | Lavi | A61M 5/2033 604/136 |
| 2004/0054326 | A1 * | 3/2004 | Hommann | A61M 5/31553 604/131 |
| 2005/0251097 | A1 * | 11/2005 | Mernoe | A61M 5/14244 604/221 |
| 2006/0124862 | A1 * | 6/2006 | Rodriquez | A61B 90/35 250/462.1 |
| 2007/0161907 | A1 * | 7/2007 | Goldman | A61B 5/0059 600/476 |
| 2007/0197968 | A1 * | 8/2007 | Pongpairochana | A61M 5/20 604/131 |
| 2010/0247513 | A1 * | 9/2010 | Agee | A61B 17/320036 424/94.67 |
| 2010/0324497 | A1 * | 12/2010 | Plumptre | A61M 5/24 604/207 |
| 2012/0035542 | A1 * | 2/2012 | Pongprairochana | A61M 5/20 604/110 |
| 2013/0218093 | A1 * | 8/2013 | Markussen | A61M 5/001 604/198 |
| 2013/0338590 | A1 * | 12/2013 | Jugl | A61M 5/31511 604/131 |

FOREIGN PATENT DOCUMENTS

| JP | S 50/38983 | 4/1975 |
|---|---|---|
| JP | 2000/513974 | 10/2000 |
| JP | 2003/530918 | 10/2003 |
| JP | 2006/511262 | 4/2006 |
| JP | 2007/522853 | 8/2007 |
| JP | 2008/503296 | 2/2008 |
| JP | 2009/523038 | 6/2009 |
| WO | 98/01173 | 1/1998 |
| WO | 2005/077441 | 8/2005 |
| WO | WO 2006/000785 | 1/2006 |
| WO | WO 2007/078447 | 7/2007 |

OTHER PUBLICATIONS

International Search Report for Int. App. No. PCT/EP2013/066775, completed Nov. 13, 2013.

* cited by examiner

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

```
Ser Pro Pro Pro Ala Gly Ser Ser Pro Gly Gly Asn Lys Leu Trp Glu
1               5                   10                  15

Ile Phe Leu Arg Val Ala Glu Glu Glu Met Gln Lys Ser Leu Asp Ser
            20                  25                  30

Thr Phe Thr Gly Glu Gly His
            35
```

AUTOINJECTOR

CROSS REFERENCE TO RELATED APPLICATIONS

The present application is a U.S. National Phase Application pursuant to 35 U.S.C. § 371 of International Application No. PCT/EP2013/066775 filed Aug. 12, 2013, which claims priority to European Patent Application No. 12180577.4 filed Aug. 15, 2012. The entire disclosure contents of these applications are herewith incorporated by reference into the present application.

TECHNICAL FIELD

The invention relates to an autoinjector for administering a medicament.

BACKGROUND

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Autoinjectors may be mechanical, electro-mechanical or fully electronic. Conventional mechanical autoinjectors may automatically provide the required force for needle insertion and medicament delivery, but may not provide additional functionality (e.g., alignment verification, injection site verification, etc.) which may be capable with electro-mechanical and fully electronic autoinjectors.

WO 2005/077441 A2 discloses a hand-held, electronically controlled injection device for injecting preset doses of liquid medications, having a housing for receiving a cartridge containing the liquid medication and having a contact surface for contacting a patient's skin; and actuator means for moving the cartridge within the housing to and from the contact surface.

U.S. Pat. No. 3,712,301 A discloses a hypodermic injector comprising a sleeve housing a cocked spring impelled plunger, a cartridge holder with a cannula pierceable stopper at the front end thereof attached to the sleeve and a cartridge with front end attached cannula in the holder wherein the rear end only of the cartridge is frictionally retained in the holder and in air tight sealing engagement therewith, the cartridge being otherwise substantially unrestrained from movement with respect to the holder, the free end of the cannula lying within the holder until the plunger is released, all to maintain cannula sterility and yet allow rapid movement of the cartridge in the holder when the plunger is operative.

U.S. Pat. No. 3,742,948 A discloses a hypodermic syringe comprising a liquid container and a needle connected thereto at one end, which assembly is incorporated in a housing, the liquid container being bounded at the other end by a piston, and an operating mechanism being present to exert a force on the piston, one or more blocking elements being present for locking the operating mechanism or the piston against movement relative to the liquid container, the housing showing a diameter transition such that when the blocking elements pass along it, they are moved radially so that the blocking is removed and the piston penetrates into the liquid container so that the liquid flows out through the needle.

EP 2 468 340 A1 discloses an auto-injector for administering a dose of a liquid medicament, comprising:—a substantially tubular front-end device adapted to contain a syringe with an injection needle and a barrel containing the dose of the medicament and comprising a needle shroud adapted to rest on the skin of a patient receiving an injection and—a reusable backend device comprising—a housing, a plunger connected to or adapted to engage a stopper providing a fluid tight seal for a distal end of the barrel,—a motor for displacing the plunger connected to the stopper, wherein the front-end device is attachable to the backend device, wherein the needle shroud is slidably arranged with respect to the injection needle and wherein an interlock switch is capable of detecting an axial position of the needle shroud.

Thus, there remains a need for an improved autoinjector.

SUMMARY

It is an object of the present invention to provide an improved autoinjector.

In an exemplary embodiment, an autoinjector according to the present invention comprises a case, a motor adapted to rotate a drive gear, and a curvi-linear plunger adapted to mate with the drive gear. The plunger includes a distal end with a resilient flange, which in a non-deflected state, abuts a proximal collar of a syringe, and, in a deflected state, advances through the proximal collar and engages a stopper in the syringe.

In an exemplary embodiment, an autoinjector according to the present invention further comprises a door adapted to cover an opening in the case when the door is in a closed position. In an exemplary embodiment, an autoinjector according to the present invention further comprises a door spring biasing the door in an open position. In an exemplary embodiment, an autoinjector according to the present invention further comprises a releasable door latch adapted to lock the door in the closed position.

In an exemplary embodiment, an autoinjector according to the present invention further comprises a gear train coupled to the motor. The gear train includes a linkage having a threaded end adapted to mate with the drive gear. The plunger may comprise a plurality of hinged links.

In an exemplary embodiment, an autoinjector according to the present invention further comprises a plurality of guides disposed within the case, and the plunger engages the guides.

In an exemplary embodiment, an autoinjector according to the present invention further comprises an energy source including a rechargeable or non-rechargeable battery.

In an exemplary embodiment, an autoinjector according to the present invention further comprises a refraction spring biasing the syringe in a retracted position within the case.

In an exemplary embodiment, an autoinjector according to the present invention further comprises a boot removal mechanism comprising a gear adapted to rotate when the door transitions from an open position to the closed position, a rack adapted to mate with the gear and axially translate when the gear rotates, resilient locking beams adapted to grip a needle boot disposed on a needle of the syringe, and a boot removal spring applying a biasing force to the rack. The boot removal spring is compressed when the door transitions from the open position to the closed position.

In an exemplary embodiment, an autoinjector according to the present invention further comprises a user interface adapted to provide at least one of visual and audible feedback and instruction.

In an exemplary embodiment, an autoinjector according to the present invention further comprises a sensor arrangement adapted to detect proximity and properties of an injection site surface. The sensor arrangement comprises at least one near infrared light emitting diode (LED) adapted to illuminate the injection site surface, and a camera adapted to obtain an image of the injection site surface. In another exemplary embodiment, the sensor arrangement comprises a projector adapted to display a pattern on the injection site surface.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
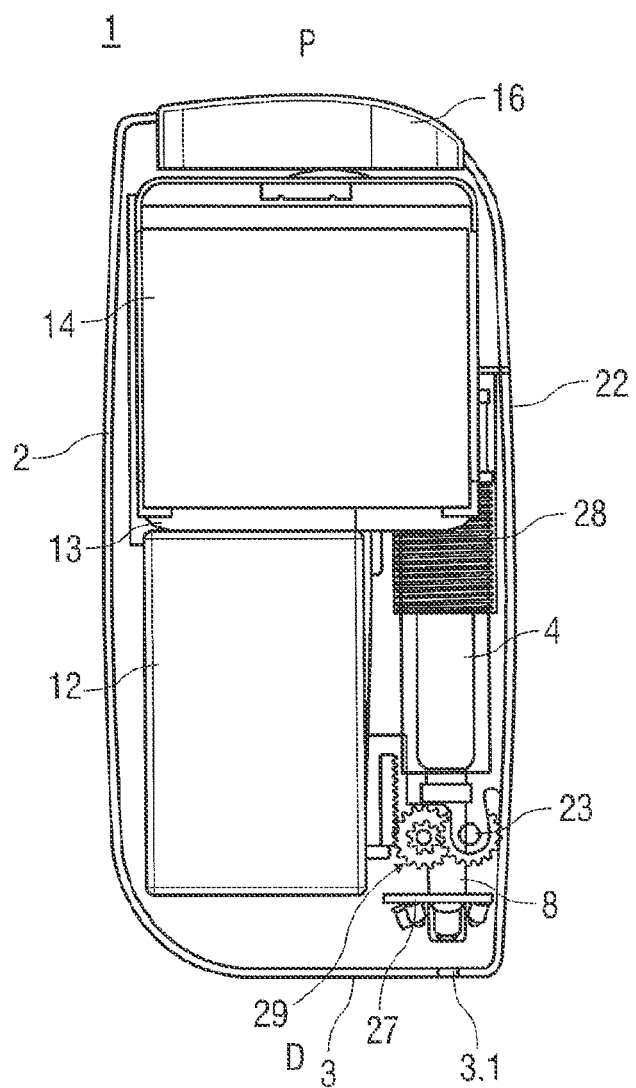
FIG. 1 is a front view of an exemplary embodiment of an autoinjector.
Figure 2:
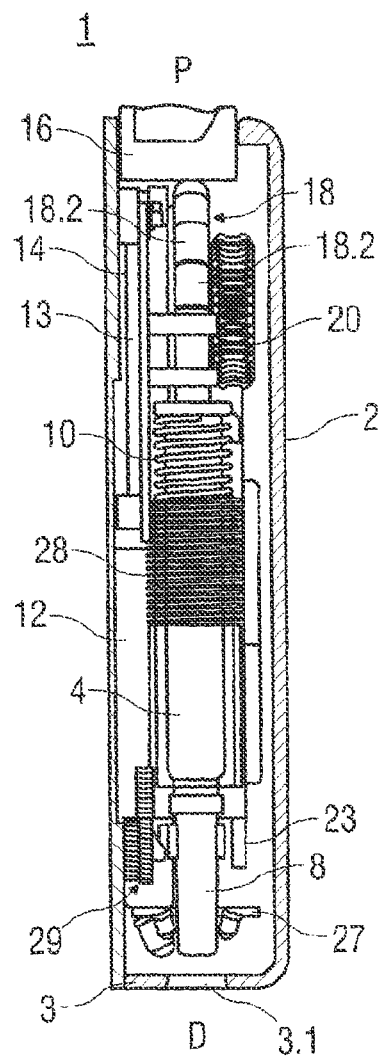
FIG. 2 is a side view of an exemplary embodiment of an autoinjector.
Figure 3:
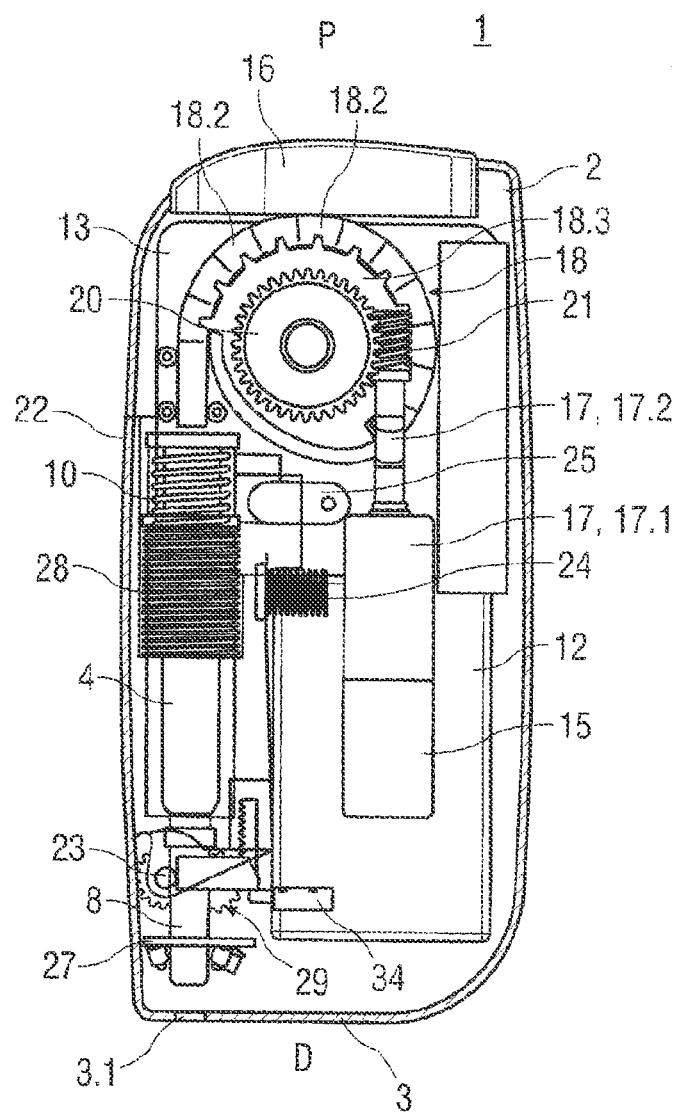
FIG. 3 is a rear view of an exemplary embodiment of an autoinjector.

FIGS. 1-3 show front, side and rear views, respectively, of an exemplary embodiment of an autoinjector 1 according to the present invention.

In an exemplary embodiment, the autoinjector 1 comprises a case 2 with a contact surface 3 intended to be applied against the skin of a patient. The case 2 may have a generally elongate, rectangular shape and may include one or more ergonomic features (e.g., finger grooves for gripping) and/or textured surfaces or skins for preventing a user's hand from slipping while using the autoinjector 1.

In an exemplary embodiment, the case 2 includes a door 22 which is configurable in an open position or a closed position. In the open position, the door 22 provides access to a syringe carrier in the case 2 that is adapted to hold a syringe or a cartridge containing a medicament. In the closed position, the door 22 may be locked. As shown in the exemplary embodiment in FIG. 1, the door 22 may be formed on a lateral side of the case 2 and rotate about a hinge between the open and closed positions. However, those of skill in the art will understand that the door 22 may be formed on any side or face of the case 2 and may rotate, slide or translate relative to the case 2 to open and close. In another exemplary embodiment, the syringe may be disposed in a channel formed in the case 2, and the syringe carrier may not be utilized.

In an exemplary embodiment, a door spring 24 may be arranged in the case 2 to bias the door 22 to the open position. A door latch 25 may be formed on the case 2 and/or the door 22 to maintain the door 22 in the closed position. In an exemplary embodiment, the door latch 25 may be rotated or deflected by a solenoid (not shown) to engage/disengage the case 2 and/or the door 22 to allow the door 22 to open and close. When the door 22 is in the open position, a used syringe may be removed from the syringe carrier and a new syringe may be inserted into the syringe carrier. A door stop 34 may be disposed in the case 2 for preventing the door 22 from rotating beyond the closed position.

Figure 4:
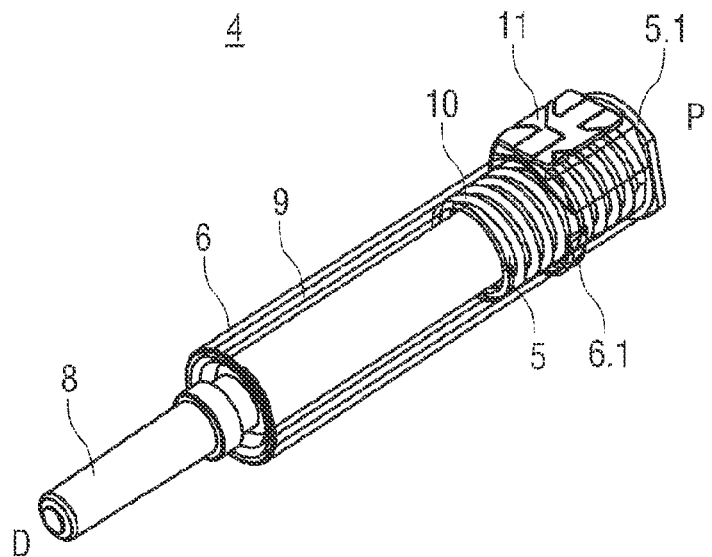
FIG. 4 is a perspective view of an exemplary embodiment of a syringe for use with an autoinjector according to the present invention.
Figure 5:
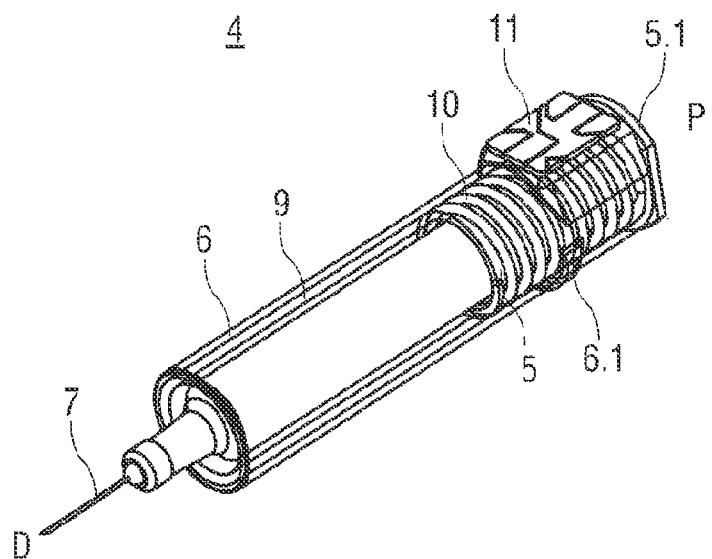
FIG. 5 is a perspective view of an exemplary embodiment of a syringe for use with an autoinjector according to the present invention.
Figure 6:
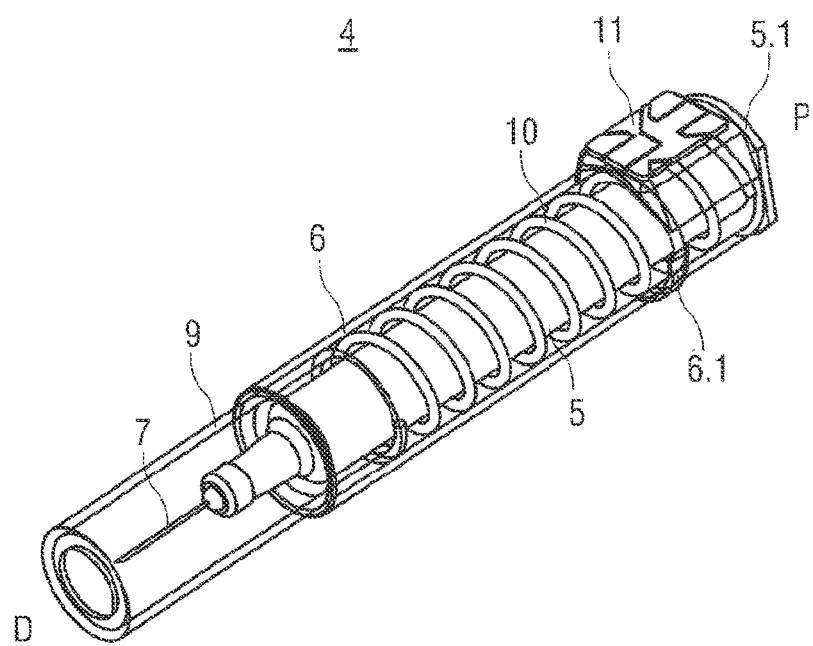
FIG. 6 is a perspective view of an exemplary embodiment of a syringe for use with an autoinjector according to the present invention.

FIGS. 4-6 show an exemplary embodiment of a syringe 4 for use with the autoinjector 1 according to the present invention. The syringe 4 includes a body 5 containing a medicament and a case 6 coupled to the body 5. The case 6 may include an attachment (e.g., hooks, snaps, etc.) which engage a finger flange 5.1 on a proximal end of the body 5. A needle shield 9 is telescopically coupled to the case 6 and is biased relative to the case 6 by a spring 10.

A needle 7 is disposed at a distal end of the body 5. A needle boot 8 is, as shown in FIG. 4, arranged on the needle 7, prior to use. FIG. 5 shows the syringe 4 with the needle boot 8 removed and the needle shield 9 in a retracted position, with the needle 7 exposed. FIG. 6 shows the syringe 4 with the needle shield 9 in an extended position, covering a distal tip of the needle 7. The needle shield 9 may lock in the extended position to prevent reuse of the needle 7.

In an exemplary embodiment, a data storage device 11 may be disposed on the syringe 4 and include data, such as a type and volume of the medicament, filling and/or expiration date of the medicament, temperature of the medicament (e.g., if there is a temperature sensor on or near the syringe 4), a manufacturer of the medicament and/or the autoinjector 1, patient data (e.g., name, physician, dosing regiment, etc.), a used/unused indicator, etc.

Referring back to FIG. 3, the autoinjector 1 includes a motor 15 adapted to drive a plunger rod 18. In an exemplary embodiment, the motor 15 may be coupled to a gear train 17, which may comprise a gearbox 17.1 and a linkage 17.2. As understood by those of skill in the art, the gear train 17 may reduce an output speed of the motor 15 to increase its torque.

In an exemplary embodiment, the linkage 17.2 includes a threaded end, such as a worm gear 21. The worm gear 21 mates with a drive gear 20. The drive gear 20 includes teeth 18.3 which mate with notches formed in links 18.2 of the plunger 18. Thus, when the motor 15 is actuated, the linkage 17.2 rotates the worm gear 21, which rotates the drive gear 20, which advances or retracts the plunger 18. Consecutive links 18.2 of the plunger 18 are hingedly attached, allowing the plunger 18 to vary between a rotated state (wrapped around the drive gear 20) and an axial state (unwrapped from the drive gear 20). In an exemplary embodiment, the links 18.2 may contain a resilient element which biases consecutive links 18.2 in the axial state. As understood by those of skill in the art, the curvi-linear plunger 18 may reduce a form factor of the autoinjector 1.

In other exemplary embodiments, the plunger 18 could be driven by, for example, a lead screw or rack and pinion geared transmission from the motor 15. In other exemplary embodiments, the plunger 18 may be arranged as a telescopic plunger or as a curved spring or tape or as a helical spring, flexible rack or segmented piston. Rollers or guide elements (shown in FIG. 9) may be disposed within the autoinjector 1 to ensure a proper path of travel of the plunger 18 as it rotates and extends.

In an exemplary embodiment, the autoinjector 1 includes an energy source 12, which may comprise one or more batteries, rechargeable or non-rechargeable. Rechargeable batteries may be recharged by connecting the autoinjector 1 to an external power supply, e.g. by plugging-in a power cable, by locating the autoinjector 1 in a docking station or by wireless inductive charging. In an exemplary embodiment, the energy source 12 is a rechargeable Lithium-Ion or Lithium-Polymer battery having a flat shape.

Figure 9:
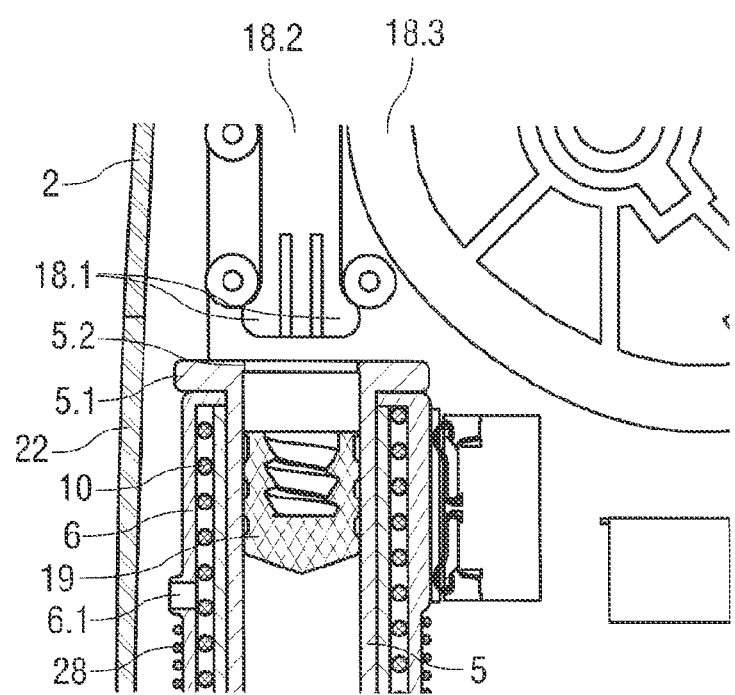
FIG. 9 is a longitudinal section of an exemplary embodiment of a plunger in an autoinjector according to the present invention.

FIG. 9 shows an exemplary embodiment of a distal end of the plunger 18. The distal end of the plunger 18 may include resilient flanges 18.1 disposed on a radial surface of the plunger 18. In an exemplary embodiment, the resilient flanges 18.1 may include ramped or rounded edges which are adapted to engage a circumferential collar 5.2 disposed on a proximal opening of the syringe body 5. In a non-deflected state, a first diameter of the resilient flanges 18.1 is larger than a second diameter of a proximal opening of the syringe body 5. When the plunger 18 initially contacts the syringe body 5, the flanges 18.1 abut the collar 5.2 and push the syringe carrier (and the syringe 4 therein) distally relative to the case 2 until the syringe carrier is stopped (e.g., against the case 2 or a distal stop positioned in the case 2) which results in insertion of the needle 7 through aperture 3.1 into the injection site. After needle insertion, the flanges 18.1 transition to a deflected state, allowing the plunger 18 to enter the syringe body 5 and push the stopper 19 to dispense the medicament.

In an exemplary embodiment, a retraction spring 28 biases the syringe carrier in a retracted position in the case 2. Thus, as the plunger 18 advances the syringe carrier distally, the retraction spring 28 is compressed. In an exemplary embodiment, the refraction spring bears on the syringe carrier. In another exemplary embodiment, the refraction spring 28 may bear on a rib 6.1 formed on the syringe case 6. In the latter exemplary embodiment, the autoinjector 1 may not utilize a syringe carrier, but include a channel adapted to receive the syringe 4. A proximal stop may be positioned in the case 2 to prevent the syringe carrier from moving proximally beyond the retracted position.

In an exemplary embodiment, the autoinjector 1 includes a data processing unit 13 which controls operation of the autoinjector 1. The data processing unit 13 may include a microprocessor and memory. As described further herein, the data processing unit 13 may process/store data and control operation of the autoinjector 1. For example, the data processing unit 13 may read data from and/or write data to the data storage device 11 on the syringe 4.

In an exemplary embodiment, at least one encoder is utilized to provide a data signal to the data processing unit 13 which is used to determine a position of the plunger 18. The encoder may be optical, mechanical, magnetic, etc. to detect a position of the plunger 18. In another exemplary embodiment, the encoder may be disposed on the drive gear 20 to sense angular rotation, and the data processing unit 13 may determine a position of the plunger 18 may on the rotation data.

Figure 7:
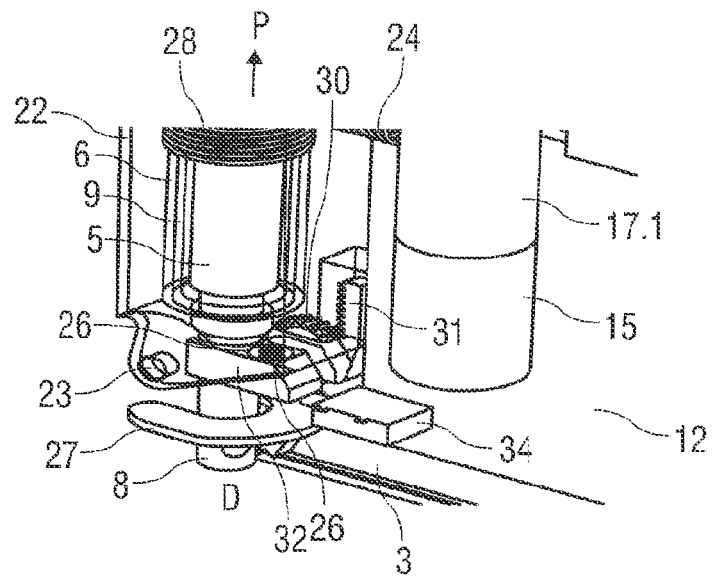
FIG. 7 is a perspective detail view an exemplary embodiment of a needle boot removal mechanism according to the present invention.
Figure 8:
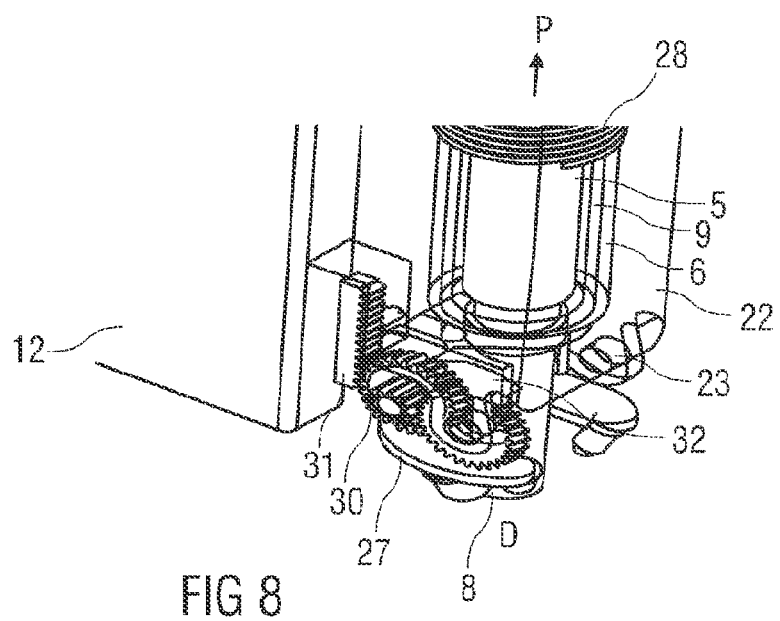
FIG. 8 is a perspective detail view an exemplary embodiment of a needle boot removal mechanism according to the present invention.

As shown in FIGS. 7 and 8, an exemplary embodiment of the autoinjector 1 may include a boot removal mechanism 29 for removing the needle boot 8 from the needle 7. In an exemplary embodiment, the boot removal mechanism 29 comprises a gear 30 which mates with a rack 31 disposed in the case 2. The gear 30 is rotated by the closing of the door 22. When the door 22 is closed, the gear 30 rotates, causing the rack 31 to advance in the proximal direction and compressing a boot removal spring 26. Resilient locking beams 32 coupled to the rack 31 are advanced over the needle boot 8 until hooks on the locking beam 32 engage a proximal end of the needle boot 8. The locking beams 32 may be retained in this position by a solenoid. Prior to an injection, the solenoid is discharged to release the locking beams 32, which under the biasing force of the boot removal spring 26, push the needle boot 8 off of the needle 7 and at least partially through the aperture 3.1 (so the user can manually remove the needle boot 8 completely). Those of skill in the art will understand that the boot removal mechanism 29 may be configured for completely removing the needle boot 8 from the needle 7 (e.g., by using a more powerful boot removal spring 26).

In an exemplary embodiment, the autoinjector 1 comprises a user interface which may include visual and acoustic components, such as LEDs, a display, a touch screen 14, a speaker, a microphone, buttons, dials, switches, etc. The data processing unit 13 may, for example, provide visual/audible cues to guide the user through an injection process, alert that a patient is due for an injection, provide distraction and/or re-assurance during the injection, providing data about the medicament (e.g., obtained from the data storage device 11), etc.

Further, the user interface may, for example, be used to configure a patient profile, configure insertion depth, injection speed, and medicament type, provide user feedback of comfort in injection, display instructions on loading or reloading of a syringe 4, authenticate a user, provide visual/audio/vibration feedback to the user to indicate injection progress, injection completion, historical user data, drug properties (e.g. use by date), etc.

In an exemplary embodiment, the user interface includes a trigger button 16 disposed on the case 2 for activating the injection process.

In an exemplary embodiment, a heater/cooling device (not illustrated) may be arranged within the case 2 for heating or cooling the medicament.

Figure 12:
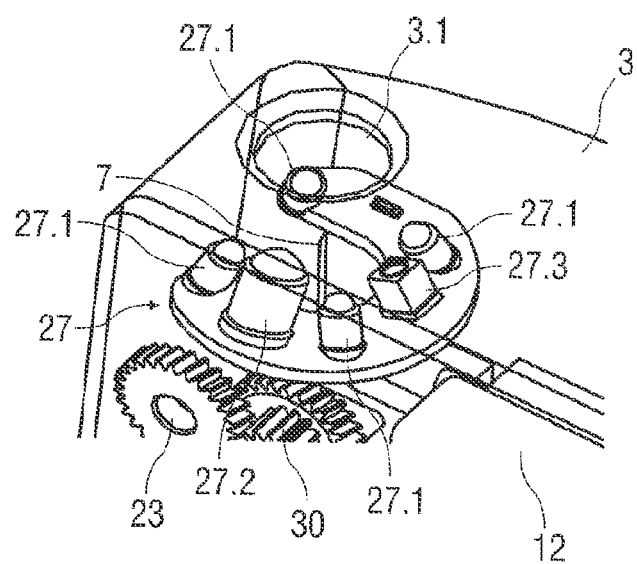
FIG. 12 is a perspective semitransparent detail view of an exemplary embodiment of an autoinjector with the needle a sensor arrangement.
Figure 13:
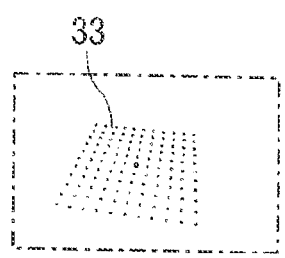
FIG. 13 is an exemplary embodiment of an illumination of a flat surface by an exemplary embodiment of a sensor arrangement according to the present invention.
Figure 14:
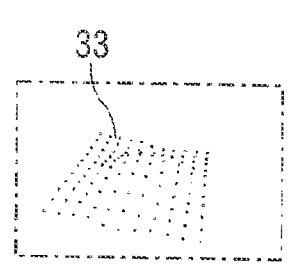
FIG. 14 is an exemplary embodiment of an illumination of a contoured surface by an exemplary embodiment of a sensor arrangement according to the present invention.

FIG. 12 shows an exemplary embodiment of a sensor arrangement 27 for use with the autoinjector 1 according to the present invention. In an exemplary embodiment, the sensor arrangement 27 is arranged in or behind the contact surface 3 for detecting veins, scar tissue, detecting contact with the injection site, and/or detecting an angle of the needle 7 with respect to the injection site. In an exemplary embodiment, the sensor arrangement 27 comprises at least one near infrared LED 27.1, a projector 27.2 and a camera 27.3. The near infrared LEDs 27.1 are arranged to illuminate the injection site, and the camera 27.3 may then obtain an image of the injection site to determine whether veins or scars are present, which would indicate an undesirable injection site. The camera 27.3 may be arranged as an integrated image sensor and lens. The projector 27.2 may comprise a laser and a diffractive optical element arranged to project a planar grid 33 onto the injection site which may be detected by the camera 27.3. Orientation of the autoinjector 1 relative to the injection site and/or injection site abnormalities may be determined from a distortion of the grid 33 detected by the camera 27.3. For example, FIGS. 13 and 14 show exemplary embodiments of the grid 33 indicating a relatively flat injection site surface (FIG. 13) and contoured injection site surface (FIG. 14), the latter of which may be undesirable for an injection.

An exemplary sequence of operation for the autoinjector 1 may be as follows:

The autoinjector 1 may provide an injection alert (e.g., based on a treatment protocol schedule) indicating it is time to administer an injection. The user interface may provide various details about the injection, e.g., day/time of last injection, medicament to inject, day/time for a subsequent injection, etc. In an exemplary embodiment, the autoinjector 1 may remain in a low-power or "sleep" mode until it provides the injection alert or is manually activated by a user.

When the autoinjector 1 is activated, the door 22 is opened and a syringe 4 is placed in the syringe carrier. As the door 22 is closed, the boot removal mechanism 29 is operated to engage the needle boot 8 on the syringe 4. After the door 22 is closed, the door latch 25 may lock the door 22 in the closed position.

When the door 22 is closed and locked, the data processing unit 13 may perform various functions such as, for example, authenticating the syringe 4 (via data on the data storage device 11), detecting medicament conditions (e.g., temperature, expiry date, etc.), and initializing mechanical, electronic and optical components of the autoinjector 1 to ensure that all are in working conditions.

In an exemplary embodiment, if the medicament is not a proper injection temperature, the heater/cooling device may heat/cool the medicament as appropriate.

The user interface may notify the user when the autoinjector 1 is ready for the injection. If, for example, the user presses the trigger button 16 a first time, the solenoid of the boot removal mechanism 29 may be discharged, and the needle boot 8 may be at least partially disengaged from the needle 7 and presented through the aperture 3.1. The user may then remove the needle boot 8, while maintaining needle safety, because the needle 7 remains fully enclosed by the case 2.

When the autoinjector 1 is positioned on an injection site, the sensor arrangement 27 may provide various information to the data processing unit 13 to determine if the injection site is adequate (e.g., aligned properly, no veins/scars detected, relatively flat surface, etc.).

Figure 10:
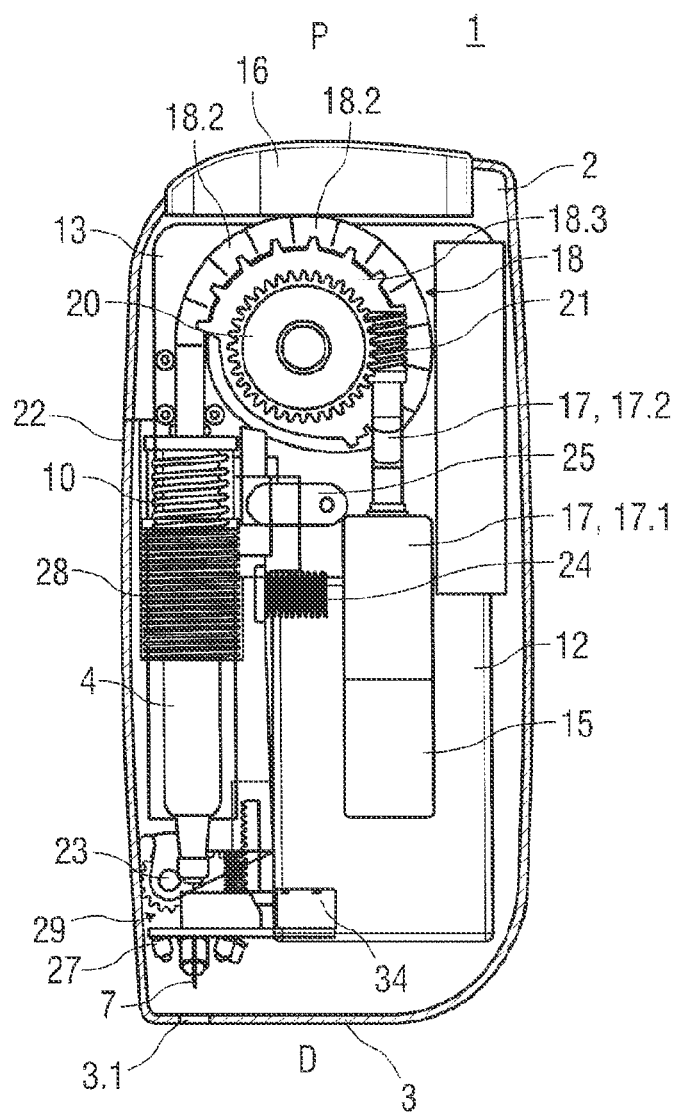
FIG. 10 is a longitudinal section of an exemplary embodiment of an autoinjector prior to needle extension according to the present invention.

As shown in FIG. 10, the autoinjector 1 is ready for the injection. When, for example, the user presses the trigger button 16, the motor 15 rotates the drive gear 20 to rotate and advance the plunger 18. The resilient flange 18.1 of the plunger engages the proximal collar 5.2 of the syringe body 5 and pushes the syringe 4 (and/or the syringe carrier) in the distal direction, compressing the retraction spring 28. When the syringe carrier abuts a distal stop in the case 2, the needle 7 is extended through the aperture 3.1 and inserted into the injection site.

Figure 11:
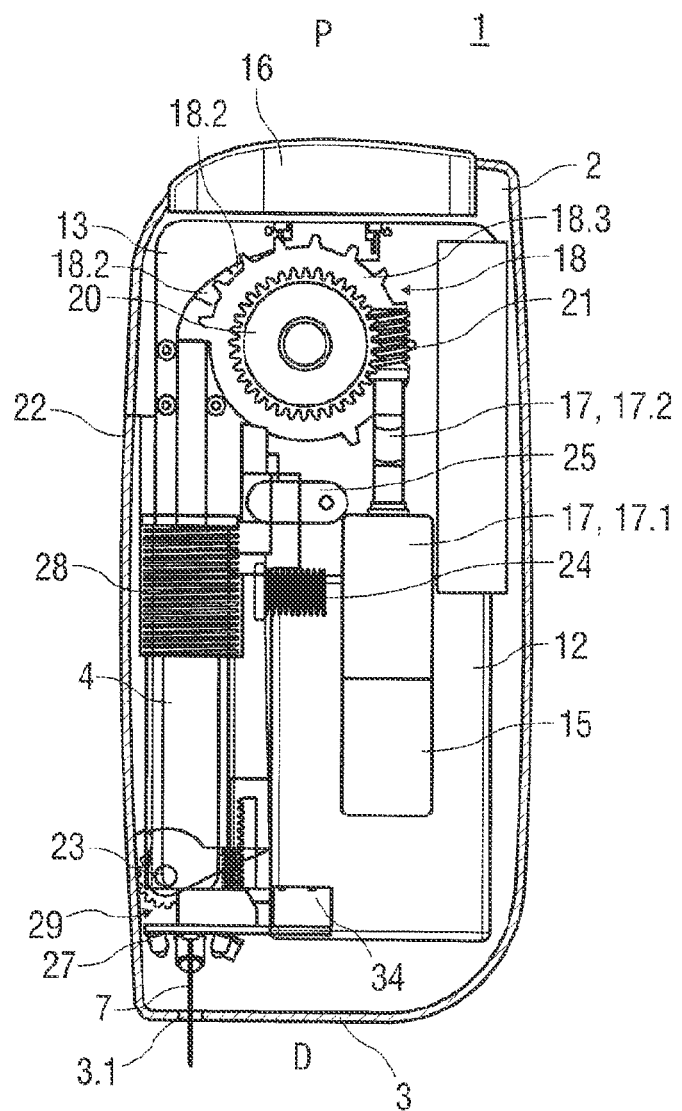
FIG. 11 is a longitudinal section of an exemplary embodiment of an autoinjector with the extended needle and a stopper advanced for emptying the syringe according to the present invention.

When the syringe carrier abuts the distal stop, the continued rotation of the drive gear 20 causes the resilient flange 18.1 to deflect, allowing the plunger 18 to enter the syringe body 5 and engage the stopper 19. The plunger 18 pushes the stopper 19 distally within the syringe body 5 to dispense the medicament through the needle 7, as shown in FIG. 11.

After the medicament has been dispensed, the motor 15 may release tension on the drive gear 20, allowing the force of the retraction spring 28 to push the syringe carrier in the proximal direction to withdraw the needle 7 from the injection site. In another exemplary embodiment, the motor 15 may reverse and rotate the drive gear 20 in an opposite rotational direction to withdraw force on the syringe carrier. In another exemplary embodiment, the drive gear 20 may disengage the motor 15, releasing force on the syringe carrier.

In an exemplary embodiment, as the needle 7 is withdrawn from the injection site, the needle shield 9 on the syringe 4 may be deployed under the force of the spring 10. For example, when the syringe 4 is at penetration depth, a latch on the needle shield 9 may be disengaged and allow the spring 10 to push the needle shield 9. However, during medicament delivery, the needle shield 9 may abut the distal end of the case 2. As the syringe 4 is retracted, the needle shield 9 may fully deploy to the extended position covering the needle 7. In an exemplary embodiment, the retraction spring 28 may push the syringe 4 a sufficient distance in the proximal direction to ensure that the needle shield 9 can achieve the extended position.

When the injection is complete, the door 22 may be opened and the used syringe 4 may be removed. Because the needle shield 9 is in the extended position, the needle 7 is fully covered, significantly reducing the risk of needle stick injuries.

Throughout the injection process, the autoinjector 1 may continuously monitor its status and provide feedback/instructions to the user via the user interface. For example, the data processing unit 13 may monitor position of the plunger 13, contact between the autoinjector 1 and the injection site, etc. For example, on detection of premature removal of the autoinjector 1 from the injection site, the autoinjector 1 may be controlled to immediately stop dispensing the drug and retract the needle 7. Controlling the needle insertion speed, dispense rate and needle insertion depth may improve patient comfort and compliance with a treatment protocol.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An autoinjector comprising:
a case;
a motor adapted to rotate a drive gear;
a curvi-linear plunger adapted to mate with the drive gear;
wherein the plunger includes a distal end with a resilient flange having ramped or rounded edges;
wherein when the motor rotates the drive gear, the plunger is advanced such that the resilient flange being in a non-deflected state is configured to engage a proximal collar of a syringe and move the syringe in a distal direction until the syringe abuts a distal stop in the case;
wherein when the syringe abuts the distal stop, a needle of the syringe is extended through an aperture and continued rotation of the drive gear is configured to cause the resilient flange to be deflected by the proximal collar resulting in a deflected state, in which the resilient flange is configured to advance through the proximal collar and engage a stopper in the syringe pushing the stopper distally to dispense a medicament through the needle.

2. The autoinjector according to claim 1, further comprising:
a door adapted to cover an opening in the case when the door is in a closed position.

3. The autoinjector according to claim 2, further comprising:
a door spring biasing the door in an open position.

4. The autoinjector according to claim 3, further comprising:
a boot removal mechanism comprising:
a gear adapted to rotate when the door transitions from an open position to the closed position;
a rack adapted to mate with the gear and axially translate when the gear rotates;
resilient locking beams adapted to grip a needle boot disposed on a needle of the syringe;
a boot removal spring applying a biasing force to the rack.

5. The autoinjector according to claim 4, wherein the boot removal spring is compressed when the door transitions from the open position to the closed position.

6. The autoinjector according to claim 2, further comprising:
a releasable door latch adapted to lock the door in the closed position.

7. The autoinjector according to claim 1, further comprising:
a gear train coupled to the motor, the gear train including a linkage having a threaded end adapted to mate with the drive gear.

8. The autoinjector according to claim 1, wherein the plunger comprises a plurality of hinged links.

9. The autoinjector according to claim 1, further comprising:
a plurality of guides disposed within the case, wherein the plunger engages the plurality of guides.

10. The autoinjector according to claim 1, further comprising:
an energy source including a rechargeable or non-rechargeable battery.

11. The autoinjector according to claim 1, further comprising:
a retraction spring biasing the syringe in a retracted position within the case.

12. The autoinjector according to claim 1, further comprising:
a user interface adapted to provide at least one of visual feedback, audible feedback, and instruction.

13. The autoinjector according to claim 1, further comprising:
a sensor arrangement adapted to detect proximity and properties of an injection site surface.

14. The autoinjector according to claim 13, wherein the sensor arrangement comprises:
at least one near infrared light emitting diode (LED) adapted to illuminate the injection site surface; and
a camera adapted to obtain an image of the injection site surface.

15. The autoinjector according to claim 14, wherein the sensor arrangement further comprises:
a projector adapted to display a pattern on the injection site surface.

* * * * *